United States Patent [19]

Groshong et al.

[11] Patent Number: 4,559,046
[45] Date of Patent: Dec. 17, 1985

[54] APPARATUS FOR INTRAVENOUS THERAPY AND HYPERALIMENTATION

[75] Inventors: LeRoy E. Groshong; Ronald J. Brawn, both of Portland, Oreg.

[73] Assignee: Catheter Technology Corporation, Salt Lake City, Utah

[21] Appl. No.: 518,069

[22] Filed: Jul. 28, 1983

Related U.S. Application Data

[60] Continuation-in-part of Ser. No. 193,629, Oct. 3, 1980, Pat. No. 4,431,426, which is a division of Ser. No. 67,753, Aug. 20, 1979, Pat. No. 4,327,722.

[51] Int. Cl.$^4$ .............................................. A61M 25/00
[52] U.S. Cl. .................................... 604/282; 128/658; 128/772; 604/105; 604/170
[58] Field of Search .............................. 128/656–658, 128/772; 604/170, 105, 280–283

[56] References Cited

U.S. PATENT DOCUMENTS

| 2,268,321 | 12/1941 | Flynn | 604/282 X |
| 2,616,429 | 11/1952 | Merenlender | 604/105 |
| 3,584,624 | 6/1971 | De Ciutiis | 604/170 |
| 4,215,703 | 8/1980 | Willson | 128/772 |
| 4,362,163 | 12/1982 | Krick | 604/280 |
| 4,388,076 | 6/1983 | Waters | 604/170 X |

FOREIGN PATENT DOCUMENTS 193885 6/1957 Sweden ................................ 604/95

Primary Examiner—Dalton L. Truluck
Attorney, Agent, or Firm—Klarquist, Sparkman, Campbell, Leigh & Whinston

[57] ABSTRACT

Apparatus for intravenous therapy including hyperalimentation comprises a flexible closed-end catheter having a valve adjacent its proximal end. It is inserted through the skin of a patient and into a vein having a suitably large flow of blood therethrough. A removable internal stiffening member comprising a doubled, twisted flexible wire abuts the proximal closed catheter end. A distal female fluid flow fitting is fixed to the distal end of the stiffening member and is releasably attached to the distal catheter end. The distal end of the catheter has a male coupler allowing releasable connection of the fluid flow fitting of the internal stiffener to a source of intravenous solution which flows by gravity or pump means through the catheter and into the vein.

2 Claims, 6 Drawing Figures

APPARATUS FOR INTRAVENOUS THERAPY AND HYPERALIMENTATION

This application is a continuation-in-part of application Ser. No. 193,629, filed Oct. 3, 1980, now U.S. Pat. No. 4,431,426 which was a divisional of application Ser. No. 67,753, filed Aug. 20, 1979, now U.S. Pat. No. 4,327,722.

BACKGROUND OF THE INVENTION

The present invention relates to the intravenous administration of nutrients and therapeutic agents to patients and, more particularly, to an apparatus for administering intravenous hyperalimentation.

Ingestion, digestion, and absorption of food and assimilation of resulting substrates into the body cell mass are vital functions of the gastrointestinal tract. These functions may be impaired in a variety of ways. For example, infants born with gastrointestinal abnormalities, adults who develop gastrointestinal diseases, burn or accident victims, cancer patients, etc., may be unable to maintain their nutritional and fluid balance by oral intake. Without proper treatment they may die from starvation and dehydration.

Traditional intravenous feeding, i.e., through relatively small veins in the limbs, has severe limitations. A patient with one of the above described maladies may initially require eight liters or more of intravenous fluid per day with enough fats, proteins, and carbohydrates to meet the body's nutritional requirements and maintain positive nitrogen balance. Beyond three liters per day, however, the excess fluid strains the cardiovascular system. A diuretic may be given so that the kidneys can process the additional fluid. However, this method is dangerous.

Another approach is to increase the concentration of nutrients in the intravenous solutions. However, such solutions cannot be dripped into a relatively small vein in the arm or leg without severe pain coupled with the risk of vein inflammation and/or thrombosis.

In the early 1960's, Dr. Stanley J. Dudrick and his colleagues developed a method of intravenous nutritional support (referred to in the medical profession as a hyperalimentation or total parenteral nutrition) by which normal growth and development as well as a positive nitrogen balance could be maintained. An open ended catheter was threaded through a moderate sized vein such as the subclavian, accessible under the collarbone, and into a very large vein, the superior vena cava. Because of the very large flow of blood through the superior vena cava, a concentrated solution delivered through the catheter is rapidly diluted, thus allowing administration of a high concentration of nutrients without risk of pain, venous inflammation, or thrombosis.

Since Dr. Dudrick's initial work, extensive research and development has been done with intravenous nutritional solutions. It has been possible to supply up to 7000 calories per day intravenously. Different apparatus and methods have evolved for short and long term intravenous therapy. With the latter, the distal end of the catheter is routed subcutaneously to an exit point midway down the anterior wall of the chest. The patient can then couple the catheter to a source of nutrients in the home and thus avoid prolonged hospitalization while still obtaining intensive nutritional therapy.

In our prior U.S. Pat. No. 4,327,722, we disclose the use of a flexible catheter closed at its proximal end but provided with a slit valve in the wall adjacent such end for fluid passage, and which catheter is inserted into a body vessel for feeding fluid to a patient. A silicone rubber sold under the trademark SILASTIC is disclosed as a suitable material for such catheters. As discussed in that patent, catheters of this type are difficult to insert into a patient because of the flexibility of the catheter, and we disclose the use of an internal stiffener such as flexible wire disposed within the catheter to facilitate its insertion.

U.S. Pat. Nos. 2,393,003; 3,128,769; 3,630,198; 3,742,950; 3,890,970; and 4,068,659; British application Nos. 2,064,963A; 2,032,278A; 1,479,396; 1,155,442; and 484,499; and European application No. 0014424, all address the problem of inserting catheters or like elements into a body.

It is an object of the present invention to provide an improved arrangement for inserting a flexible catheter into a patient.

More particularly, it is an object of the invention to provide an arrangement of catheter and inserting stiffener which permits fluid to be passed through or withdrawn from the catheter as the same is inserted into a patient.

Another object is to provide an improved stiffener that may be withdrawn easily from a catheter after it has been inserted without disturbing the position of the catheter.

It is an object of the present invention to provide an extremely flexible and soft closed-end catheter with an internal stiffening member releasably attached and a distal fluid flow adapter such that the proximal end of the stiffener abuts the closed catheter end allowing facile insertion of the soft flexible catheter by pulling the catheter into place and such that fluid may be infused into or body fluids withdrawn from the catheter through the adapter while the internal stiffening member is in place.

It is yet another object of the present invention to provide a catheter construction allowing determination of venous pressure, preferably in the superior vena cava (central venous pressure), of the vessel in which the catheter tip is positioned without allowing blood reflux into the catheter and without the need for additional apparatus or manometers.

SUMMARY OF THE INVENTION

In accordance with the present invention, a catheter is provided formed of an extremely soft, flexible material such as a silicone rubber. The catheter is closed at its proximal end, but one or more valves through which fluid may flow are provided in the wall of the catheter adjacent such end. A rigid sleeve is fixed in the distal end of the catheter. To facilitate insertion of the catheter into a patient, the catheter is provided with a removable internal stiffener comprising in the preferred form a doubled, twisted flexible wire. The doubled end of the wire abuts the closed proximal catheter end. The opposite end of the stiffener is connected to a coupling member which is removably engaged to the distal end of the catheter. The coupler permits a source of fluid to be connected to the catheter during its insertion or allows attachment of a syringe means to withdraw body fluid through the catheter during insertion. The doubled wire stiffener is of such flexibility it can bend to conform to the bends of the body vessel or vessels in which the catheter is inserted, but stiff enough such that by pushing on the wire it will advance with the catheter through an inserting instrument and through a vessel pulling the catheter along with it. After insertion, the coupler may be detached from the catheter and removed, withdrawing the stiffener from the catheter. The twisted configuration of the stiffener provides numerous advantages as set forth in detail hereinafter. After removal of the coupler and stiffener, the remaining portion of the catheter, if it is used for long term intravascular therapy, may be inserted under the skin of the patient using the technique illustrated and described in our U.S. Patent No. 4,327,722. If the catheter is inserted as described in that patent for short term intravascular therapy, the distal end of the catheter may be connected to a source of fluid after removal of the coupler and stiffener.

DESCRIPTION OF THE PREFERRED EMBODIMENTS

The term "proximal end" when used in reference to a needle, sleeve, or catheter, refers to the forward end thereof which is inserted into the patient's body. The term "distal end" when used in reference to a needle, sleeve, or catheter, refers to the rearward end thereof which is situated externally of the patient's body.

Figure 1:
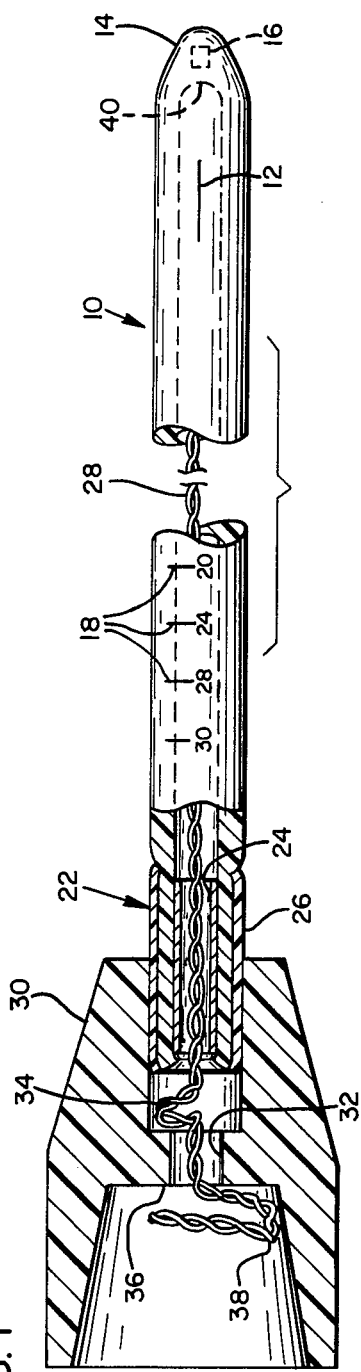
FIG. 1 is a fragmentary view of a catheter of the invention showing the same with the stiffener in place.
Figure 2:
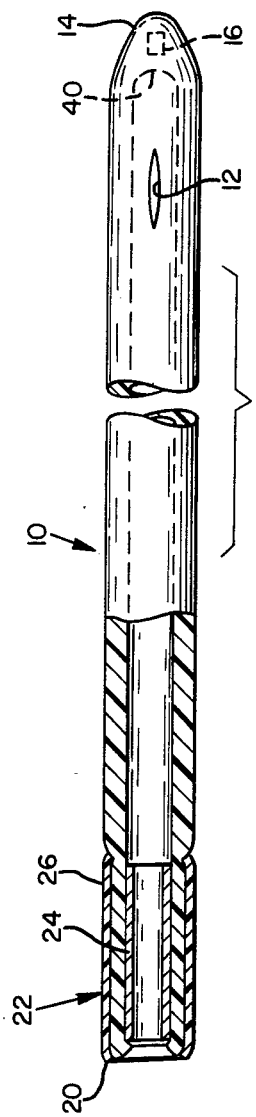
FIG. 2 is a fragmentary view of the catheter itself, partly in section.
Figure 3:
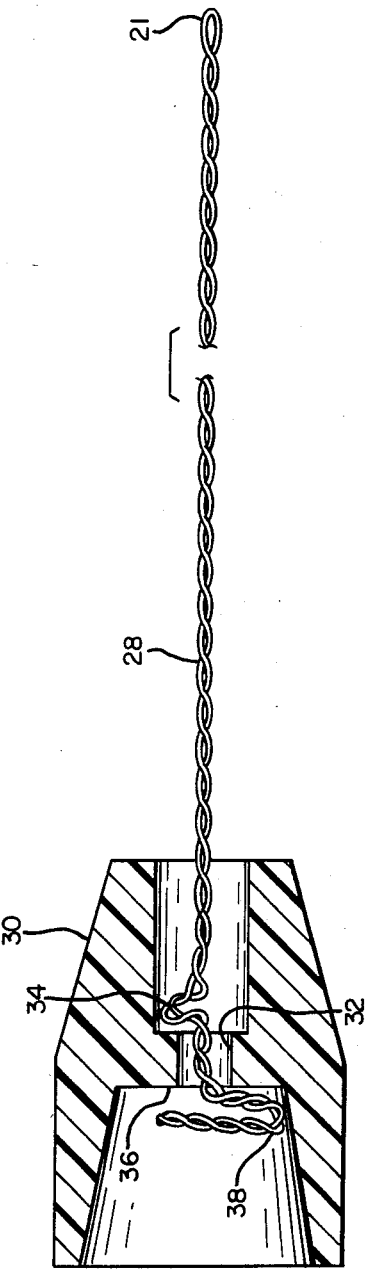
FIG. 3 is a view of the stiffener and adapter.
Figure 4:
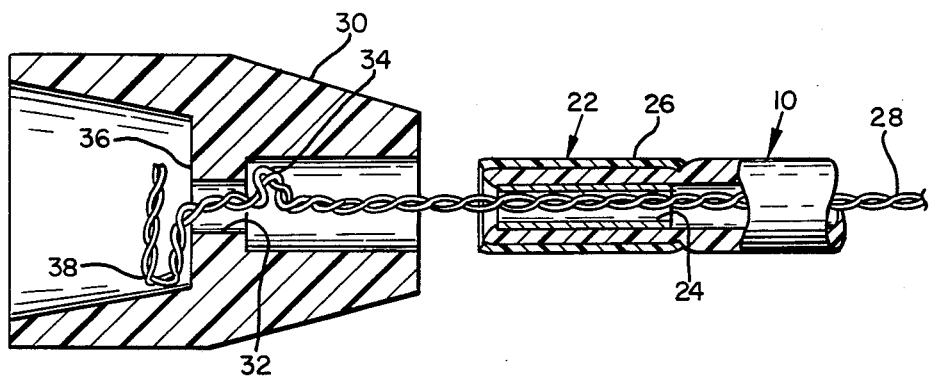
FIG. 4 is a fragmentary view of the proximal end of the catheter illustrating how the stiffener is removed.

Referring first to FIGS. 1–3, the catheter 10 which is to be inserted into the patient is made of a durable, flexible, biocompatible material such as, but not necessarily, silicone rubber. One suitable material is sold under the registered trademark SILASTIC. Preferably the catheter is translucent so that the physician can determine the presence of air bubbles within the catheter. When used for short term intravenous therapy, the catheter preferably has sufficient length to extend from the skin of the patient to a vein which will not be adversely affected by the intravenous therapy or therapeutic agent administered. In the case of administration of concentrated hyperalimentation fluids, this length should be sufficient, for example, to extend from the site of insertion to the superior vena cava. The length will depend upon the size of the patient and the intended therapy to be administered. When used for long term intravascular therapy, the catheter preferably has sufficient length to extend from the superior vena cava to the deltopectoral groove or anterior lateral neck and further to a point midway down the anterior wall of the chest. These requirements and the selection of a suitable length will be known to those of skill in the art of central venous catheterization.

The catheter must have a relatively small outside diameter so that it can be readily inserted into a vein, such as the subclavian vein, without causing undue trauma to the vein and the surrounding tissues. Preferably the catheter has an outside diameter no greater than four millimeters. The inside diameter of the catheter must be large enough to permit solution to flow therethrough at a rate sufficient to allow the required amount of nutrients or therapeutic agents to be delivered. An example of a suitable size is an outside diameter of 2.2 mm and an inside diameter of 1.3 mm.

The catheter has a valve 12 (FIG. 1) adjacent its proximal end. The valve may be formed by one or more individual slits precisely cut into the catheter wall. Multiple slits may be circumferentially spaced. As shown in FIG. 2, the valve 12 opens when the fluid pressure inside the catheter is greater than the fluid pressure outside the catheter by a predetermined amount, and similarly opens inwardly when the pressure outside exceeds the interior pressure by a predetermined amount. The minimum amount of pressure needed to open the valve may be varied from catheter to catheter by varying the number of slits, length of the slits, the thickness of the catheter wall, or the elasticity of the catheter wall, all as described in greater detail in our copending application Ser. No. 491,258, filed May 3, 1983.

The catheter preferably has a coating of anticoagulant substances, such as sodium heparin, on its internal and external surfaces to prevent the formation of blood clots thereon. The surfaces defined by the slits 12 should preferably be coated in this manner to prevent blood clots from forming on the valve openings.

The proximal end 14 of the catheter is preferably rounded or pointed to facilitate insertion and advancement of the catheter in the vein. It may contain a quantity of radiopaque material 16, such as barium sulfate, so that the position of the proximal end of the catheter within the patient can be determined by x-ray. Alternatively, the entire catheter may be impregnated with a radiopaque material or a longitudinal stripe of radiopaque material may be provided within the catheter. The catheter preferably has a metric scale indicia 18 which can be observed by the physician to determine the extent to which the catheter has been inserted.

The distal end 20 of the catheter is open and a tubular male coupler 22 is integrally fitted to the distal end. Preferably the coupler consists of a rigid but thin walled internal bushing 24 which fits in the catheter lumen and a sleeve 26 of thermoplastic material slightly longer than the bushing which fits over the catheter material, extending slightly beyond the internal bushing at each end, and which is shrink fitted over the catheter material and the internal bushing to form a rigid and durable male coupler. Preferably the outer diameter of the bushing 24 is no greater than the internal diameter of the catheter tubing and the tubing is stretched over the bushing during application of the external thermoplastic sheath so that the total diameter of the male coupler 22 is no greater than the nominal outer diameter of the catheter tubing.

To facilitate insertion of the catheter 10 into a vein, a removable stiffener 28 is positioned in the catheter during insertion such that the proximal end of the stiffener abuts the closed proximal catheter end 14. Referring to FIGS. 1 and 3, the stiffener 28 is preferably secured in a suitable manner to a fluid flow adapter 30 which fits upon the male coupler 22 such that fluid can be passed into or withdrawn from catheter 10 during its insertion into a patient.

As illustrated, the stiffener extends through the throat 32 of the adapter and is formed with an offset bend 34 on one side of the throat defining flange 36 with the distal end of the stiffener likewise bent in an offset 38 on the opposite side of the flange 36. Thus the stiffener is locked to the adapter so that when the adapter is pulled off the coupler 22 and moved away therefrom, the stiffener 28 will be withdrawn from the catheter 10. The stiffener enables the very soft, flexible catheter to be pulled into place from the proximal end during the insertion process while allowing fluid infusion into and withdrawal from the catheter during the insertion process by means of a syringe attached to the stiffener fluid flow adapter. This capability is critical in order to confirm the catheter is positioned within a blood vessel during the insertion process. The internal stiffener preferably has considerable flexibility so that during insertion the catheter can easily be advanced through serpiginous vascular channels without risk of vascular perforation. In addition, the stiffener must be sufficiently flexible so that it will not perforate or pass through the proximal closed end of the catheter. Preferably the catheter stiffener has a flexibility such that a 12-inch (30.5 cm) length when held at one end deflects about 13 or 14 cm from the horizontal at the free end. It is important that the proximal end 21 of the stiffener be blunt and rounded so that perforation of the closed catheter end is prevented. It is additionally desirable that there be a cup or concavity 23 in the inner surface of the closed catheter end allowing the stiffener securely to seat in the proximal end of the catheter. Furthermore, it is desirable that the area of engagement of the stiffener and the internal catheter wall be small in order to facilitate removal of the stiffener from the catheter after successful catheter insertion. Thus, the stiffener preferably has a surface configuration such as to provide only point or small area contact with the internal wall of the catheter. In accordance with the illustrated embodiment, the stiffener 28 comprises a length of flexible medical grade stainless steel 0.008" diameter wire bent back on itself at the proximal end and helically wound toward the distal end of the catheter.

An important advantage of the folded wire configuration of the stiffener is that the folded end 21 provides a rounded surface to engage the catheter end and thereby minimize the possibility of a puncture.

Alternatively, the stiffener 28 could comprise an extruded plastic material having polygonal or other suitable non-circular cross-sectional configuration.

Figure 5:
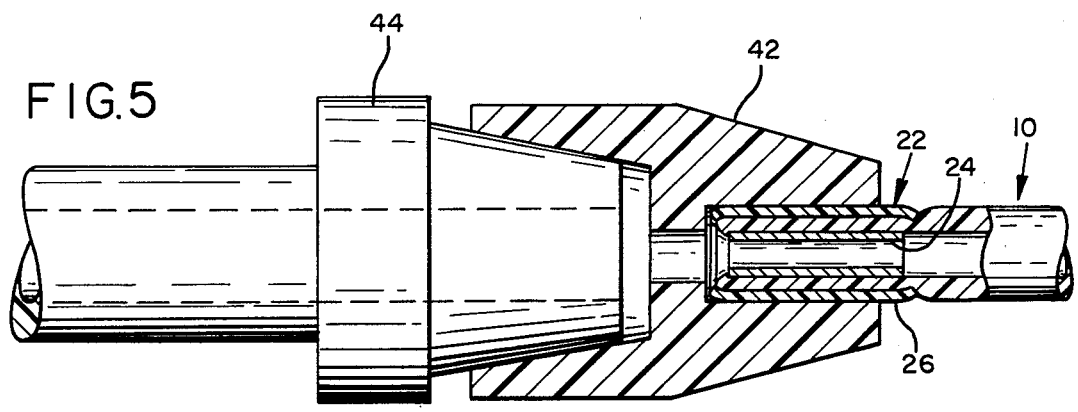
FIG. 5 is a fragmentary view of the proximal end showing a fluid flow adapter connected to the proximal end of the catheter with a standard intravenous set male fitting connected thereto.
Figure 6:
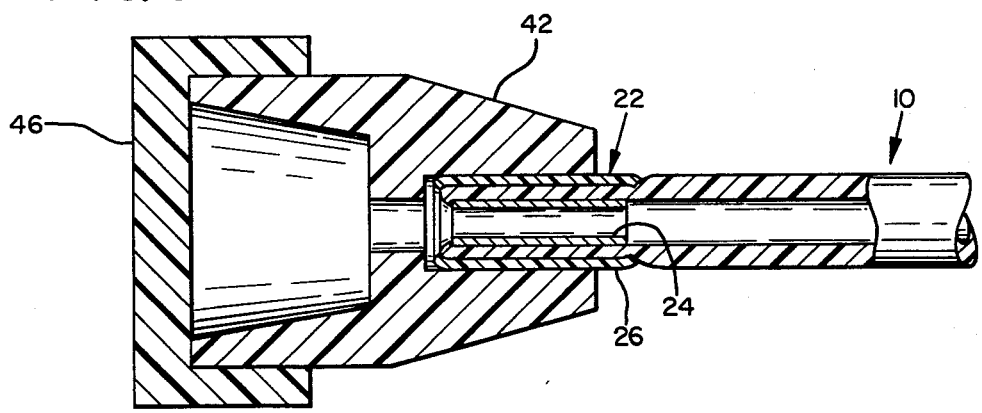
FIG. 6 is a view similar to FIG. 5 with the male fitting removed and a cap replacing it.

Referring to FIG. 5, after removal of the fluid flow adapter 30 and stiffener 28, the male coupler 22 may be connected to a fluid flow adapter 42 fashioned to be coupled to the standard male fitting 44 of an intravenous administration set. The fluid flow adapter 42 may also accept a cap 46 (FIG. 6) or heparin lock which may be utilized when no intravenous fluid therapy is being administered.

As will be apparent, the catheter may be inserted by any of the usual methods, for example, a sleeve may be inserted into a desired vessel as described in our U.S. Pat. No. 4,327,722 and the catheter then threaded through the sleeve into the vessel utilizing the force applied through the stiffener 28 to pull the catheter into the vessels. If desired, the catheter may be filled with a desired fluid, e.g., saline solution, prior to insertion. Also by withdrawing fluid from the catheter by means of a hypodermic cylinder and plunger connected to the adapter 30, a check of the catheter proximal end position may be made. A show of blood will confirm it is within the desired blood vessel and that an accidental puncture has not been made. When the proximal end is in place, the adapter 30 is disconnected and the stiffener 28 withdrawn. Thereafter, the fluid flow adapter 42 may be applied and connected to a suitable source of intravascular fluid.

If long term intravascular therapy is to be carried out, a suitable length of catheter 10 may be initially selected. After insertion into the body of the proximal end 14 of the catheter and withdrawal of the stiffener 28, the exterior portion of the catheter may be inserted subcutaneously in some suitable manner, as, for example, by use of a passer as described in our U.S. Pat. No. 4,327,722.

Having described a preferred embodiment of the invention, it will be perceived that it permits of modification in detail and arrangement.

We claim:

1. In combination, a flexible catheter having a closed proximal end and an open distal end, and a stiffener to facilitate the insertion of said catheter into a body vessel, said stiffener comprising a helically twisted, doubled flexible wire positioned with its doubled end adjacent the closed proximal end of the catheter, said wire being twisted throughout its length, the distal end of said stiffener extending to the distal end of said catheter, whereby force applied to said stiffener towards the proximal end thereof will cause the proximal end of said stiffener to pull the proximal end of said catheter through a body vessel when the same are inserted therein, said stiffener being unattached to said catheter whereby it may be withdrawn from the catheter after insertion of the catheter into a body vessel.

2. The combination of claim 1 including a fluid flow adapter releasably connected to the distal end of said catheter and fastened to the distal end of said stiffener, whereby fluid may be passed into or drawn from said catheter through said adapter as said catheter is inserted into a body vessel and said stiffener may be withdrawn from said catheter by removal of said fluid flow adapter.

* * * * *